US012778950B2

(12) United States Patent
Psarrakis et al.

(10) Patent No.: US 12,778,950 B2
(45) Date of Patent: Nov. 3, 2026

(54) ORAL GLIPTIN COMPOSITIONS AND METHOD FOR PREPARATION THEREOF

(71) Applicant: PHARMA-DATA RESEARCH AND DEVELOPMENT SINGLE MEMBER S.A., Lavrio (GR)

(72) Inventors: Ioannis Psarrakis, Lavrio (GR); Konstantinos Lioumis, Lavrio (GR)

(73) Assignee: PHARMA-DATA RESEARCH AND DEVELOPMENT SINGLE MEMBER S.A. (GR)

( * ) Notice: Subject to any disclaimer, the term of this patent is extended or adjusted under 35 U.S.C. 154(b) by 0 days.

(21) Appl. No.: 19/189,609

(22) Filed: Apr. 25, 2025

(65) Prior Publication Data

US 2025/0302828 A1 Oct. 2, 2025

Related U.S. Application Data

(63) Continuation of application No. 18/587,175, filed on Feb. 26, 2024, now Pat. No. 12,295,953, which is a continuation of application No. 17/771,387, filed as application No. PCT/EP2020/079945 on Oct. 23, 2020, now Pat. No. 11,944,621.

(30) Foreign Application Priority Data

Oct. 24, 2019 (EP) .................................... 19205219

(51) Int. Cl.

| | |
|---|---|
| ***A61K 31/4985*** | (2006.01) |
| ***A61K 9/00*** | (2006.01) |
| ***A61K 9/08*** | (2006.01) |
| ***A61K 47/10*** | (2017.01) |
| ***A61K 47/12*** | (2006.01) |
| ***A61K 47/14*** | (2017.01) |
| ***A61K 47/18*** | (2017.01) |
| ***A61K 47/20*** | (2006.01) |
| ***A61K 47/26*** | (2006.01) |
| ***A61K 47/36*** | (2006.01) |
| ***A61K 47/38*** | (2006.01) |

(52) U.S. Cl.

CPC ........ *A61K 31/4985* (2013.01); *A61K 9/0053* (2013.01); *A61K 9/08* (2013.01); *A61K 47/10* (2013.01); *A61K 47/12* (2013.01); *A61K 47/14* (2013.01); *A61K 47/183* (2013.01); *A61K 47/20* (2013.01); *A61K 47/26* (2013.01); *A61K 47/36* (2013.01); *A61K 47/38* (2013.01)

(58) Field of Classification Search

CPC ...... A61K 9/08; A61K 31/4985; A61K 47/38; A61K 47/10; A61K 47/20

See application file for complete search history.

(56) References Cited

U.S. PATENT DOCUMENTS

| | | | |
|---|---|---|---|
| 7,326,708 | B2 | 2/2008 | Cypes et al. |
| 11,944,621 | B2 | 4/2024 | Psarrakis et al. |
| 2024/0285619 | A1 | 8/2024 | Psarrakis et al. |

FOREIGN PATENT DOCUMENTS

| | | | | |
|---|---|---|---|---|
| EP | 1354882 A1 | 10/2003 | | |
| EP | 1532149 A2 | 5/2005 | | |
| EP | 1828192 A2 | 9/2007 | | |
| EP | 2923694 A1 | 9/2015 | | |
| WO | WO-2007078726 A2 | 7/2007 | | |
| WO | WO-2012131005 A1 | * | 10/2012 | ......... A61K 31/4985 |
| WO | WO-2015044880 A1 | * | 4/2015 | ............. A61K 45/06 |
| WO | WO-2015071859 A1 | 5/2015 | | |

OTHER PUBLICATIONS

Dodge et al.; "Medications as a source of paraben exposure"; 2015; Reproductive Toxicology; 52: 93-100; http://dx.doi.org/10.1016/j.reprotox.2015.02.002 (Year: 2015).*

Szymczyk et al.; "Effect of Polysorbates on Solids Wettability and Their Adsorption Properties"; Jul. 8, 2018; Colloids Interfaces; 2, 26; pp. 1-15; doi:10.3390/colloids2030026 (Year: 2018).*

Agarkhed et al.; "Effect of Polysorbate 80 Concentration on Thermal and Photostability of a Monoclonal Antibody"; 2013; AAPS PharmSciTech; 14(1): 1-9; DOI:10.1208/s12249-012-9878-0 (Year: 2013).*

Agarkhed, Meera et al.: Effect of Polysorbate 80 Concentration on Thermal and Photostability of a Monoclonal Antibody. AAPS PharmSciTech. 14(1):1-9 (2013). doi: 10.1208/s12249-012-9878-0 PMCID: PMC3581664.

Bull City Flavors, 'Forest Fruit Flavor-FA.' [Online] [retrieved on Sep. 29, 2023]. Retrieved from the Internet: https://www.bullcityflavors.com/forest-fruit-flavor-fa/.

Dodge, Laura E. et al.: Medications as a Source of Paraben Exposure. Reprod. Toxicol. 52:93-100 (2015). doi: 10.1016/j.reprotox.2015.02.002.

PCT/EP2020/079945 International Search Report mailed Apr. 29, 2021.

Szymczyk, Katarzyna et al.: Effect of Polysorbates on Solids Wettability and Their Adsorption Properties. Colloids Interfaces 2(3):26 (2018); https://doi.org/10.3390/colloids2030026.

* cited by examiner

*Primary Examiner* — Timothy P Thomas

(74) *Attorney, Agent, or Firm* — Wilson Sonsini Goodrich & Rosati

(57) ABSTRACT

Described herein are liquid oral gliptin compositions. The liquid oral gliptin compositions may comprise a gliptin or a pharmaceutically acceptable salt thereof, an artificial non-sugar alcohol sweetening agent, and liquid oral gliptin compositions may have a sugar alcohol content of less 25 w/v %. The liquid oral gliptin compositions described herein have improved taste and stability. Further provided herein are methods of manufacturing liquid oral gliptin compositions.

22 Claims, No Drawings

ORAL GLIPTIN COMPOSITIONS AND METHOD FOR PREPARATION THEREOF

CROSS REFERENCE TO RELATED APPLICATIONS

This application is a continuation of U.S. patent application Ser. No. 18/587,175, filed Feb. 26, 2024, which is a continuation of U.S. patent application Ser. No. 17/771,387, filed Apr. 22, 2022, now U.S. Pat. No. 11,944,621, issued Apr. 2, 2024, which is a national phase application under 35 U.S.C § 371 of International Application No. PCT/EP2020/079945, filed Oct. 23, 2020, which claims priority to EP 19205219.9, filed Oct. 24, 2019; each of which are incorporated by reference in their entirety.

BACKGROUND OF THE INVENTION

The invention relates to an oral gliptin solution and to a method for the preparation thereof.

Gliptins are enzymes that catalyses the inactivation of glucagon like peptide-1 (GLP-1) and are known as DPP-IV inhibitors. The enzymatic action involves competitive inhibition of the enzyme DPP-IV, thereby increasing the endogenous concentration of GLP-1, which further augments insulin secretion and improves the glycemic profile of patients with diabetes.

Currently, gliptins such as sitagliptin, vildagliptin, saxagliptin, teneligliptin, alogliptin, and linagliptin are available as conventional tablet dosage forms. Oral liquid compositions, however, provide better patient compliance, and offer advantages such as more reproducible bioavailability, rapid absorption from the gastrointestinal tract, and an option of a flexible dosing regimen based on body weight or body surface area.

As gliptins are generally bitter in taste, any oral liquid formulation must provide sufficient taste-masking to result in a palatable formulation. One solution to taste-masking of gliptins has been proposed in WO2015/044880, describing an aqueous solution having a significant amount of sugar alcohol, e.g., 45 w/v % xylitol or other sugar alcohols. However, the formulation of WO20151044880 appeared to still have bitter aftertaste; no market authorisation for an oral gliptin formulation has yet been obtained.

An aqueous composition comprising a substituted xanthine as a DPP-IV inhibitor and hydroxypropyl cellulose as thickener is described in EP1532149. This composition is intended either as suspension for intravenous administration or as solid composition in the form of coated tablets, capsules powders for oral administration or as suppository for anal administration. An oral liquid solution comprising a gliptin and the concomitant problems of bitter taste is not addressed in EP1532149.

EP1354882 describes a DPP-IV inhibitor that can be formulated into an oral formulation such as a syrup comprising water, sugar, sorbitol, fructose, glucose, oil, an antiseptic and a flavour.

EP1828192 describes an oral formulation comprising a non-gliptin DPP-IV inhibitor, citric acid, sodium hydroxide and a flavouring agent.

WO2015/071859 describes an oral formulation comprising a DPP-IV inhibitor that disintegrates within 3 minutes after oral administration.

WO2007/078726 describes a pharmaceutical composition comprising a DPP-IV inhibitor and 25-94 w/w % metformin hydrochloride.

Improved oral solution formulations of gliptins are desired, having acceptable taste-masking and acceptable stability.

DETAILED DESCRIPTION

It has now surprisingly been found that an aqueous liquid gliptin composition without the bitter after taste can advantageously be obtained when the composition has a sugar alcohol content of less than 25 w/v % and comprises gliptin or a pharmaceutically acceptable salt thereof, and an artificial non-sugar alcohol sweetening agent. Therefore, the invention provides such an aqueous liquid gliptin composition. As will be explained in more detail below, it was surprisingly found that the presence of sugar alcohols, in particular above 25 w/v % has a negative effect on taste. In addition, it has been surprisingly been found that the presence of a thickener further improves taste-masking, while also improving stability. The term “thickener” or “thickening agent,” as used herein interchangeably, means a pharmaceutically acceptable excipient that increases the viscosity of a liquid composition.

The term ‘sugar alcohol’ is well-known in the art and refers to carbohydrates, having at least 3 consecutive carbon atoms, each carbon atom having covalently linked thereto a hydroxyl group, with the general formula $HOCH_2(CHOH)_nCH_2OH$, and are classified as polyols. The most simple sugar alcohol is ethylene glycol, where n in the formula is 0. Sugar alcohols are often used in medicine as thickener or sweetener or a combination thereof. Examples of sugar alcohols include xylitol, mannitol, glycerol, erythritol, threitol, arabitol, ribitol, mannitol, sorbitol, galactitol, fucitol, iditol, inositol, volemitol, isomalt, maltitol, lactitol, maltotritol, maltotetraitol, and polyglycitol.

The term ‘aqueous’ means that more than 50 v/v % of the solvent is water, preferably more than 80 v/v %, more preferably more than 90 v/v %, and even more preferably more than 95 v/v %. A cosolvent can be used if desired. The composition is however preferably void of a co-solvent.

The gliptin is preferably chosen from the group, consisting of sitagliptin, vildagliptin, saxagliptin, teneligliptin, alogliptin, linagliptin and pharmaceutically acceptable salts and esters thereof. The term gliptin or any of the gliptins mentioned herein encompass the acceptable salts and esters thereof. The gliptin preferably comprises sitagliptin.

Pharmaceutically acceptable salts or esters may be prepared from an inorganic acid or an organic acid selected from the group comprising of hydrochloric acid, hydrobromic acid, hydroiodic acid, nitric acid, carbonic acid, bicarbonic acid, sulphuric acid, phosphoric acid, bisulphonic acid, oxalic acid, formic acid, acetic acid, propionic acid, succinic acid, glycolic acid, gluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, mesylic acid, salicyclic acid, p-hydroxybenzoic acid, phenylacetic acid, mandelic acid, embonic acid, methanesulfonic acid, ethanesulphonic acid, benzene sulphonic acid, pantothenic acid, 2-hydroxyethanesulphonic acid, toluene sulfonic acid, sulphanilic acid, cyclohexylaminosulphonic acid, stearic acid, alginic acid, salicyclic acid, galactaric acid, and galacturonic acid. The sitagliptin is preferably in the form of a chloride or phosphate salt, in particular the chloride salt (sitagliptin-HCl). It is however also possible to incorporate another sitagliptin salt in the composition, such as e.g. the dihydrogenphosphate salt, as is known from U.S. Pat. No. 7,326,708.

Gliptins as used in the solutions of the present invention may be present as crystalline, amorphous, anhydrous, hydrous, solvates, prodrugs, chelates, or complex forms. The dose of any of the gliptins may depend upon the individual drug used in the liquid pharmaceutical solution of the present invention.

The composition preferably comprises 1-5 w/v % gliptin, more preferably 2-4 w/v % even more preferably 2.5-3.5 w/v %.

It is found that by incorporation of a thickener, the taste-masking even improves, as well as the stability of the composition. This will be more explained in the examples below. Increased viscosity by the thickener may act to minimize the undesired after taste as a result of less contact of the composition with the tonsils of the tongue upon oral administration. Although some sugar alcohols may have some thickening effect, the term “thickener” or “thickening agent” as used herein preferably excluded sugar alcohols.

The thickening agent is preferably selected from the group consisting of hydroxyethyl cellulose, hydroxypropyl cellulose, sodium alginate, sodium carboxy methylcellulose, gellan gum, xanthan gum, acacia, guar gum, locust bean gum, gum tragacanth, starch, carbopols, methylcellulose, polyvinylpyrrolidone, polyethylene oxide polymer and combinations thereof. Preferably, the thickening agent is selected from the group consisting of hydroxyethylcellulose, sodium alginate, hydroxypropylcellulose, gellan gum, polyethylene oxide polymer, and combinations thereof.

The composition preferably comprises 0.1-2.5 w/v % thickener, more preferably 0.1-2.0 w/v %. even more preferably 0.1-1.0 w/v % thickener. The optimal concentration of thickener may differ among different thickeners. Some thickener, such as hydroxyethylcellulose will result in a high-viscous composition at a concentration of 0.6 w/v % or higher, which may result in an undesired mouthfeel as assessed by a user, that may qualify the taste of the composition as less optimal, not due to the lack of taste-masking, but due to the prominent undesired mouthfeel. For that reason, the optimal amount of thickener can be established empirically.

In some embodiments, the thickening agent is hydroxyethylcellulose in an amount of from about 0.1% w/v % to about 0.8% w/v %, preferably of from about 0.4% w/v % to about 0.6% w/v %. In embodiments where sodium alginate is the thickening agent, it is preferably in an amount of from about 0.2% w/v % to about 0.4% w/v %. In embodiments where hydroxypropylcellulose is the thickening agent, it is preferably in an amount of from about 0.1% w/v % to about 0.3% w/v %, and most preferably in an amount of about 0.2% w/v %. In embodiments where gellan gum is the thickening agent, it is preferably present in an amount of from about 0.1% w/v % to about 0.3% w/v %, and most preferably in an amount of from about 0.1% w/v % to about 0.2% w/v %. In embodiments where carboxymethylcellulose is the thickening agent, it is preferably in an amount of from about 0.1% w/v % to about 0.4% w/v %. In embodiments where polyethylene oxide polymer is the thickening agent, it is preferably present in an amount of from about 0.5% w/v % to about 2.0% w/v %, and most preferably in an amount of from about 1.0% w/v % to about 2.0% w/v %.

The composition comprises an artificial non-sugar alcohol sweetening agent. As already indicated above, the composition comprises less than 25 w/v % sugar alcohols. An artificial non-sugar alcohol sweetening agent is an additive that provides sweet taste like that of sugar but derived through manufacturing of plant extracts or processed by chemical synthesis, not belonging to the sugar alcohols as defined above. Such artificial sweeteners contain often far less energy than regular sugars used for sweetening. Such sweeteners can also be referred to as ‘non-nutritive sugar-based sweeteners’, i.e. having no significant nutritional value and not sugar based. Herein, a chemically treated sugar is an artificial sweetener. For example, sucralose is produced by controlled chlorination of the sugar saccharose. Sucralose is therefore an artificial sweetener, that is derived from a sugar, but the sweetener is defined herein as ‘non-sugar based’. Artificial non-sugar alcohol sweeteners do not have the thickening effect of sugar alcohol and have a significantly higher sweetening power.

Because of the high sweetening power of artificial non-sugar alcohol sweetening agents, it has become possible to provide for a composition wherein the off-taste of the gliptin is sufficiently masked, while retaining a workable volume of the composition, without the presence of a significant amount of sugar alcohol, while also achieving acceptable shelf stability.

The amount of artificial non-sugar alcohol sweetening agent is preferably chosen such, that it corresponds with the sweetening power in the solution of 500-1000 w/v % saccharose. This means that, e.g., in case sucralose is used as the sole artificial sweetening agent, the amount of sucralose is 0.83-1.67 w/v %, as the sweetening power of sucralose is 600 times that of saccharose. More preferably, the amount of non-sugar alcohol sweetening agent in the solution has a sweetening power that corresponds with the sweetening power of 800-900 w/v % saccharose.

In another embodiment, the composition preferably comprises 1-5 w/v % artificial non-sugar-alcohol sweetening agent, more preferably 2-4 w/v % even more preferably 2.5-3.5 w/v %.

Suitable artificial non-sugar alcohol sweetening agents, (i.e. non-nutritive sugar-based sweeteners) are selected from the group consisting of sucralose, sodium saccharin, acesulfame-K, aspartame, alitame, cyclamate, stevioside, glycyrrhizin, neohesperidin, dihydrochalcone, thaumatin, and combinations thereof. The sweetener preferably comprises sucralose and/or saccharin, more preferably a combination of sucralose and sodium saccharin, preferably in a weight ratio of about 2-1.5:1, or a combination of sucralose and acesulfame-K, preferably in a weight ratio of 3-4:1.

In an attractive embodiment, the composition comprises: 0.8-2.0 w/v % sucralose and 0.2-1.0 w/v % saccharin, or 0.8-2.0 w/v % sucralose and 0.2-1.0 w/v % acesulfame K.

In order to improve the stability of the sitagliptin, the composition preferably comprises an antioxidant, preferably in an amount of 0.01-0.10 w/v %.

Any pharmaceutically acceptable antioxidant can be used, but preferred antioxidants are selected from the group consisting of butylated hydroxyl anisole, sodium metabisulfite, butylated hydroxyl toluene, tocopherol, ascorbyl palmitate, ascorbic acid, sodium sulphite, sodium thiosulfate, propyl gallate, and combinations thereof. The antioxidant preferably comprises butylated hydroxyl anisole (BHA) or metabisultphite.

The pH of the composition is preferably between 3-8, mor preferably between 4-7, even more preferably between 5-6, and most preferably between 5.5 and 5.8.

As explained above, the composition described herein incorporates an artificial non-sugar alcohol sweetening agent, and a low amount of sugar alcohols, in order to successfully mask the gliptin off-taste. In a preferred embodiment, the composition comprises less than 20 w/v % sugar alcohols, more preferably less than 10 w/v %, even more preferably less than 5, 4, 3, 2 or 1 w/v % and is most preferably void of sugar alcohols.

It has also been observed that the presence of polyalkylene glycols, such as polyethylene glycol or polypropylene glycol, may have a negative effect on the taste masking and mouthfeel of the composition, Therefore, the composition preferably comprises less than 10 w/v % polyalkylene glycols, more preferably less than 5 w/v % and is most preferably void of polyalkylene glycols.

The aqueous gliptin solution may comprise a co-solvent, preferably a glycol, more preferably a glycol chosen from the group consisting of propylene glycol, dipropylene glycol, ethylene glycol, butylene glycol, hexylene glycol and combinations thereof. It has been found that the solubility of some thickeners is better in such a co-solvent than in water. the thickener can be dissolved in the co-solvent before being added to the aqueous composition. As the presence of a co-solvent is less preferred in view of taste-masking efficiency, the co-solvent is preferably present in low amount of 0.5-10 w/v % of the total solution, more preferably 1-5 w/v %. The co-solvent preferably comprises a $C_{3-6}$ alkylene glycol., more preferably propylene glycol. More preferably, the co-solvent is propylene glycol.

The aqueous oral gliptin solution preferably comprises one or more pharmaceutically acceptable excipients selected from the group consisting of flavouring agents, buffering agents, preservatives, chelating agents, wetting agents, pH-adjusting agents, colouring agents, and combinations thereof. The skilled person will be aware of suitable pharmaceutically acceptable excipients The composition preferably comprises flavouring agent. The flavouring agent is preferably selected from the group comprising of forest fruits flavour, grapefruit, orange, lime, lemon, mandarin, pineapple, strawberry, raspberry, mango, passion fruit, kiwi, apple, pear, peach, apricot, cherry, grapes, banana, cranberry, blueberry, black currant, red currant, gooseberry, lingonberries, cumin, thyme, basil, camille, valerian, fennel, parsley, camomile, tarragon, lavender, dill, bargamot, *salvia*, aloe vera balsam, spearmint, peppermint, *eucalyptus*, and combinations thereof, the flavour preferably comprising forest fruit flavour. The flavour is provided as a mixture with adjuvants. A preferred mixture is provided as mixture of maltodextrin, modified starch, lactic acid, benzyl alcohol, ethyl alcohol, ethyl butyrate, propylene glycol. The flavour can e.g. be frambinon crystals or maltol, or any of the above. Such a flavour is available as mixture with artificial sweeteners sold under the trade name POLISUCRA, Spain.

The composition preferably comprises 0.1-0.5 w/v % flavouring agent.

The composition preferably comprises a buffering agent. Suitable buffering agents are selected from the group consisting of sodium citrate, sodium bicarbonate, potassium bicarbonate, magnesium hydroxide, magnesium lactate, aluminium hydroxide, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, sodium acetate, potassium metaphosphate, magnesium oxide, magnesium carbonate, magnesium silicate, calcium acetate, calcium glycerophosphate, calcium hydroxide, calcium lactate, calcium carbonate, calcium bicarbonate, and combinations thereof. The buffering agent more preferably comprises a citrate, preferably trisodium citrate dihydrate.

The composition preferably comprises 0.1-1.0 w/v % buffering agent.

The composition preferably comprises a preservative. The preservative is preferably selected from the group consisting of methyl paraben, ethyl paraben, propyl paraben, butyl paraben, benzoic acid, sodium benzoate, benzyl alcohol, sorbic acid, potassium sorbate, and combinations thereof, the preservative preferably comprising methylparaben, in particular sodium methyl paraben.

The composition preferably comprises 0.1-0.5 w/v % preservative.

The composition preferably comprises a chelating agent. The chelating agent is preferably selected from the group consisting of disodium edentate salt (EDTA), tartaric acid, malic acid, citric acid, and combinations thereof, the chelating agent preferably comprising disodium edentate salt.

The composition preferably comprises 0.01-0.1 w/v % chelating agent.

The composition preferably comprises a wetting agent.

The wetting agent is preferably selected from the group consisting of sodium lauryl sulphate, sorbitan esters of fatty acids, sorbitan monolaurate, sorbitan monooleate, sorbitan trioleate, sorbitan monopalmitate, sorbitan monostearate, sorbitan tristearate, ethylene oxide-propylene oxide block copolymers, lecithins, oleic acid and oleic acid salts, propylene glycol monostearate and monolaurate, glycerol monostearate and monooleate, fatty alcohol-polyethylene glycol ethers, fatty acid-polyethylene glycol esters, sodium dodecyl sulphate, dioctyl sodium sulphosuccinate, ethoxylated mono- and diglycerides, sucrose fatty acid esters, fatty acid salts, ethoxylated triglycerides, polyoxyethylated hydrogenated castor oil, sterol, and combinations thereof, the wetting agent preferably comprising sorbitan monooleate, more preferably polysorbate 80.

The composition preferably comprises 0.05-0.25 w/v % wetting agent.

The composition preferably comprises a pH adjusting agent. A pH agent can be used if the envisaged pH is not reached by the mere combination of the other ingredients.

The pH-adjusting agent is preferably selected from the group comprising of hydrochloric acid, acetic acid, ammonia solutions, monoethanolamine, diethanol-amine, triethanolamine, meglumine, sodium citrate, citric acid, lactic acid, phosphoric acid, propionic acid, sulphuric acid, tartaric acid, potassium bicarbonate, potassium citrate, potassium hydroxide, sodium bicarbonate, sodium borate, and sodium hydroxide. The pH-adjusting agent preferably comprises citric acid.

The composition preferably comprises 0.02-0.15 w/v % pH adjusting agent.

The aqueous oral gliptin solution may also comprise a colouring agent. Suitable pharmaceutically acceptable colouring agents are known in the art. The colouring agent is preferably selected from the group consisting of natural colouring agents; natural juice concentrates; pigments such as titanium dioxide, iron oxide, and zinc oxide; and combinations thereof.

The solution of the invention may also comprise one or more additional suitable additional antidiabetic drugs, preferably selected from the group comprising of acarbose, miglitol, repaglinide, nateglinide, glibenclamide, gliclazide, glimepiride, glipizide, tolbutamide, metformin, phenformin, rosiglitazone, pioglitazone, troglitazone, farglitazar, englitazone, darglitazone, isaglitazone, reglitazar, rivoglitazone, liraglutide, muraglitazar, peliglitazar, tesaglitazar, canagliflozin, dapagliflozin, remogliflozin, sergliflozin, and pharmaceutically acceptable salts or esters thereof. Further, the additional antidiabetic drug may comprise a DPP-IV inhibitor.

The gliptin is preferably dissolved in the composition as described herein, more preferably completely dissolved. The composition is preferably a solution.

For practical commercial use, pharmaceutical formulations will have at least 18 months, and preferably at least 24 months of shelf life. Preferably, the pharmaceutical compositions are stable at room temperature and do not require refrigeration. Sitagliptin compositions of the invention, therefore, provide at least 95% sitagliptin after 18 months storage at 25° C. at a relative humidity of 60%, preferably at least 95% sitagliptin after 24 months storage at 25° C. at a relative humidity of 60%. Sitagliptin compositions of the invention provide less than 1.5% total impurities after 18 months storage at 25° C. at a relative humidity of 60%, preferably less than 1.5% total impurities after 24 months storage at 25° C. at a relative humidity of 60%.

As noted, compositions of the invention that include thickener provide improved taste-masking as well as improved stability. Compositions that comprise thickener provide at least 97% sitagliptin after 9 months storage at 25° C. at a relative humidity of 60%, or after storage at 5° cat relative humidity of 60%, and preferably at least 98% sitagliptin after 9 months storage at 25° C. at a relative humidity of 60%, or after storage at 5° cat relative humidity of 60%. Compositions that comprise thickener provide less than 1.0% total impurities after 9 months storage at 25° C. at a relative humidity of 60%, or after storage at 5° cat relative humidity of 60%.

Compositions of the invention preferably provide less than 0.20% total impurities after 2 months storage at 25° C. at a relative humidity of 60%, and/or less than 0.55% total impurities after 4 months storage at 25° C. at a relative humidity of 60%, and/or less than 0.70% total impurities after 6 months storage at 25° C. at a relative humidity of 60%, and/or less than 1.0% total impurities after 9 months storage at 25° C. at a relative humidity of 60%.

The invention also relates to a method for the preparation of an aqueous oral composition of any of the preceding claims, comprising the steps of:

(i) heating 80-95 v/v % of the water to 40-65° C.,
(ii) admixing, the buffering agent (if present), antioxidant (if present), and the chelating agent (if present),
(iii) optionally, cooling down to 25-35° C.,
(iv) admixing, if present, the wetting agent,
(v) admixing sweetener, and, if present, preservative agent, and optionally the pH adjusting agent or a portion thereof,
(vi) admixing the gliptin,
(vii) if necessary, adjust the pH to the envisaged value by addition of pH adjusting agent,
(viii) admixing the thickening agent,
(ix) optionally, homogenising the mixture obtained in step (viii),
(x) if necessary, adjust the final volume by adding from the rest of the water of step (i),
(xi) optionally, filter through 1 to 10 μm pore sieve, and
(xii) filling in an appropriate container.

The wetting agent is preferably added before the sweeteners and the sitagliptin. However, addition of the wetting agent can also be done later, in particular as last addition step, such as before adjustment to the final volume. The thickening agent can also be admixed together with one or more of the other ingredients. In an attractive embodiment, in particular in case the thickener does not dissolve well in the composition, the thickening agent is dissolved in water or the co-solvent before admixing. It is preferred to dissolve the thickener in water and admix with the said aqueous solution in step (viii).

In a preferred embodiment, cooling step (iii) is performed.

Preferably the homogenisation step (ix) is performed.

Step (xi) is preferably performed as well, and it is preferred to use a 1 to 5 μm pore sieve.

Step (v) preferably comprises the application of nitrogen bubbling into the solution with a rate of 5-10 litres per minute, preferably 6-8 litres per minute for a time of 2-10 minutes.

The above steps are preferably performed in consecutive order.

The invention will now be further illustrated by way of non-limiting examples.

EXAMPLES

As Sitagliptin may degrade under the influence of light, the process was performed shielded from direct sunlight. The process was otherwise performed using regular manufacturing equipment. The basic steps are as follows:

Materials and Methods

Preparation of Oral Sitagliptin Compositions

The following ingredients were used in the preparations described below:

Sitagliptin: Sitagliptin HCl, Biocon, India.

Sweetener/flavouring mix: 55.25 w/w % Sucralose E955, 29.75 w/w % sodium saccharin E954, 15 w/w % forest fruits flavour (mixture of maltodextrin, modified starch, lactic acid, benzyl alcohol, ethyl alcohol, ethyl butyrate, frambinon crystals, propylene glycol) (sold under the trade name POLISUCRA 7477), Kemtia, Spain.

Alternative sweetening mix: 65 w/w % Sucralose E955, 35 w/w % sodium saccharin E954, 15 w/w % forest fruits flavour (supra) (sold under the trade name POLISUCRA 7478), Kemtia, Spain.

Maltitol solution (Maltilite 55/75 Pharma, Tereos Syral SAS, France); Lycasin 55/75, Roquette, France).

Aqueous sorbitol solution 70% (Meritol 160 Pharma, Tereos, France)

Acesulfame Potassium (Ace K, Prinova, UK)

Sucralose (Nutrilo, Germany)

Saccharin sodium (JMC Corporation, Japan)

Sweetening mix: Magnasweet MM100, Mafco US

Banana flavour: Banana liquid 3870, International Flavours & Fragrances, US.

Lemon flavour: Lemon 821 liquid, International Flavours & Fragrances, US.

Lime mint: International Flavours & Fragrances, US.

Fruit Mix: Tutti Frutti liquid 6693, International Flavours & Fragrances, US.

Masking flavour: Masking flavour 4626 powder, International Flavours & Fragrances, US.

the product Methyl paraben sodium sold under the trademark: EMPROVE®), Merck, US.

the product Hydroxyethylcellulose sold under the trademark: NATROSOL™ 250 HX, Ashland, US.

Microcrystalline cellulose: Avicel 591, Dupont, US.

the product Sodium alginate sold under the trademark: MANUCOL® LKX, FMC Corporation, US the product Hydroxypropylclulose sold under the trademark: KLUCEL™ HF, Ashland, US Gellan Gum: CEROGA Type 700 F, Roeper, Germany the product Carboxymethylcellulose sold under the trademark: BLANOSE™ CMC 7LP, Ashland, US the product Polyethylene oxide polymer sold under the trademark: POLYOX™ N750, Dow Chemicals, US Citric acid anhydrous, Citrique Belge, Belgium.

Propylene glycol, BASF, Germany.

Glycerol (glycerine 4808, 99.5%), Oleon NV, Belgium).

Disodium edentate salt (EDTA), Scl ITALIA, Italy.

Polysorbate 80, Mosselman, Belgium.

Butyl Hydroxy Anisole (BHA), Merck, US.

Metabisulphite sodium, Merck, Germany.

Trisodium citrate dihydrate, Jungbunzlauer, Switzerland

Formulas 1-8 as given in table 1 were prepared as follows. The envisaged ingredients were weighted.

For formulas 1, 2, 4, 6 and 8, BHA was admixed to 92-95% of purified water that was preheated to 52-55° C., allowing a slightly clear, somewhat cloudy solution to be formed. For formulas 3, 5 and 7, metabisulphite was admixed to 92-95% of purified water at room temperature.

EDTA and citrate were admixed under continuous mixing and a cloudy solution was obtained.

Thereafter, the mixture was cooled down to 25-30° C.

When the obtained mixture contains BHA, Polysorbate 80 was admixed. In case the obtained mixture contains metabisulphite, no polysorbate was added.

The final volume of the composition was adjusted to the final volume of 100 ml by adding the rest of purified water.

The composition was filtered through a 10-μm sieve and filled in type Ill amber glass vials and kept at 5° C. until further use.

Formula 2 has also been prepared without antioxidant (Formula 2A), without both antioxidant and thickener (Formula AT), with 0.1 w/v % sodium metabisulphite instead of Butyl Hydroxy Anisole (Formula 2B).

Further, the composition as described in example 5b of WO2015/044880 has been prepared according to the teaching therein (Formula R5B).

Analytical Procedures

Instrumentation: Shimadzu (Duisburg, Germany) Prominence Series HPLC-DAD modular system consisting of: a

TABLE 1

| Ingredient | Function | Formula 1 (g) | Formula 2 (g) | Formula 3 (g) | Formula 4 (g) | Formula 5 (g) | Formula 6 (g) | Formula 7 (g) | Formula 8 (g) |
|---|---|---|---|---|---|---|---|---|---|
| Sitagliptin | API | 2.900 | 2.900 | 2.900 | 2.900 | 2.900 | 2.900 | 2.900 | 2.900 |
| Sweetening/ favouring mix | Sweetener/ flavour | 2.000 | 2.000 | 0.400 | 0.400 | — | — | — | — |
| Maltitol | Sweetener | — | — | — | — | 24.000 | 24.000 | 7.000 | 7.000 |
| Sorbitol | Sweetener | — | — | — | — | 24.000 | 24.000 | — | — |
| Acesulfame potassium | Sweetener | — | — | — | — | — | — | 0.100 | 0.100 |
| Sucralose | Sweetener | — | — | — | — | — | — | 0.800 | 0.800 |
| Saccharia sodium | Sweetener | — | — | — | — | — | — | 0.100 | 0.100 |
| Sweetening mix | Sweetener | — | — | — | — | — | — | 0.500 | 0.500 |
| Banana flavour | Flavour | — | — | — | — | 0.200 | 0.200 | 0.200 | 0.200 |
| Lemon flavour | Flavour | — | — | — | — | 0.250 | 0.250 | 0.250 | 0.250 |
| Lime mint | Flavour | — | — | — | — | — | — | 0.100 | 0.100 |
| Fruit mix | Flavour | — | — | — | — | — | — | 0.100 | 0.100 |
| Masking flavour | Flavour | — | — | — | — | 0.100 | 0.100 | 0.100 | 0.100 |
| Methyl paraben sodium | Antimicrobial agent | 0.200 | 0.200 | 0.200 | 0.200 | 0.200 | 0.200 | 0.200 | 0.200 |
| Hydroxyethyl-celllose | Thickening agent | 0.400 | 0.400 | 0.400 | 0.400 | 0.400 | 0.400 | 0.500 | 0.500 |
| Microcrystalline cellulose | Thickening agent | — | — | — | — | 1.000 | 1.000 | 1.000 | 1.000 |
| Citric acid anhydrous | Acidifying agent | 0.143 | 0.143 | 0.075 | 0.075 | 0.075 | 0.075 | 0.075 | 0.075 |
| Propylene glycol | Cosolvent | 3.500 | — | — | — | — | — | — | — |
| Glycerol | Cosolvent | — | — | — | — | 24.000 | 24.000 | 7.000 | 7.000 |
| EDTA | Antioxidant synergist | 0.050 | 0.050 | 0.050 | 0.050 | 0.050 | 0.050 | 0.050 | 0.050 |
| Polysorbate 80 | Non-ionic surfactant | 0.100 | 0.100 | — | 0.100 | — | 0.100 | — | 0.100 |
| BHA | Antioxidant | 0.020 | 0.020 | — | 0.020 | — | 0.020 | — | 0.020 |
| Metabisulphite | Antioxidant | — | — | 0.100 | — | 0.100 | — | 0.100 | — |
| Trisodiuam citrate dihydrate | pH Buffering agent | 0.500 | 0.500 | 0.500 | 0.500 | 0.500 | 0.500 | 0.500 | 0.500 |
| Purified water | Solvent | qs to 100 ml | qs to 100 ml | qs to 100 ml | qs to 100 ml | qs to 100 ml | qs to 100 ml | qs to 100 ml | qs to 100 ml |

Methyl paraben sodium, citric acid, and the envisaged sweeteners and flavours were admixed.

The obtained mixture was homogenized for 5-6 minutes.

Sitagliptin HCl was added at 22-25° C. and the mixture was very well mixed.

The pH was checked to have the envisaged value of between 5.5-5.9.

A premix obtained by dissolving the product hydroxyethylcellulose sold under the trademark NATROSOL™ 250HX in polyethylene glycol (formula 1) or in water (formulas 2-8) to obtain a thick clear solution was admixed.

The obtained mixture was homogenized for 5-6 minutes.

DGU-20A5 mobile phase degasser, an LC-20 AD micro dual piston pump, an SIL-20ACHT autosampler, a CTO-20AC column oven, an SPD-M20 UV/Vis photodiode array detector, and a personal computer with Shimadzu LC Solutions software (v.1.11 SP1) installed for the system control, and the data record and process.

Reagents:

HPLC—grade water ($H_2O$) (resistivity >18 MΩ cm) by deionization and distillation;

Acetonitrile (ACN) (Fisher Chemical, Germany, HPLC grade);

Orthophosphoric acid (Fisher Chemical, Germany); Potassium

Dihydrogen phosphate (LANH:NER)

Determination of Sitagliptin Content

Column: EC NUCLEODUR 100-5 CN, 150×4.6 mm, 5 μm (Lot: 34512022-SN: E13090360)

Reference solution: Sitagliptin Hydrochloride working standard

Diluent: ACN/0.1% $H_3PO_4$: 5/95

Standard solution of sitagliptin (0.1 mg/ml): An accurately weighted quantity of Sitagliptin HCl working standard of 21.8 mg (equivalent to 20 mg sitagliptin base) was transferred into a 20 mL volumetric flask. 10 ml of diluent was added, followed by mixing and sonicating for 2 min. Diluent was added to adjust the envisaged volume, followed by mixing and homogenizing. Of this solution, 1.0 ml was transferred into a 10 ml volumetric flask, diluted to volume with diluent and vortexed/mixed to homogenize. Two different standard solutions were prepared.

Test solution (0.1 mg/ml): An accurately weighed quantity of sample suspension equivalent to 50 mg Sitagliptin base was transferred into a 50.0 ml volumetric flask. 20 mL diluent was added. The obtained mixture was vortexed/mixed to dissolve and sonicated for 2 min. Of the obtained solution, 1.0 ml was transferred into a 10 mL volumetric flask, diluted to the envisaged volume with diluent and vortexed/mixed to homogenize. The obtained solution was filtrated through a RC 0.45 μm filter and filled in a HPLC vial. Two different sample solutions were prepared.

Chromatographic Parameters

Mobile phase: ACN: Buffer pH 2.0/18:82 v/v

Buffer pH 2.0: 1.36 g potassium dihydrogen phosphate was weighted in 1000 ml of HPLC water. The pH was adjusted to 2.0 with orthophosphoric acid (85%). The buffer was filtrated through a 0.45-μm membrane filter.

Injection volume: 20 μl

Flow rate: 0.8 ml/min

Column temperature: 30° C.

Autosampler temperature: 25° C.

Run time: 35 minutes

Quantification wavelength: 205 nm

Procedures: Six replicates of sitagliptin standard solution (before proceeding system suitability criteria should be met) and 2 replicates of verification standard solution were injected. The recovery against the mean areas of the two standard solutions were calculated. (The recovery should be between 98-102%). One replicate of each sample solution was injected.

System Suitability Criteria:

The 6 replicates of the standard solution were used:

a) % RSD≤2.0% b) Tailing Factor≤1.5 c) Plate Count>2000

Calculation of the % Content of Sitagliptin by the Equation:

$$\% \text{ Assay} = \frac{A_{test}}{A_{std}} \times \frac{W_{std}\,x\,50}{W_{test}\,x\,20\,x\,LC} \times d \times \%\ P$$

wherein $A_{test}$ is the area of the Sitagliptin peak in the chromatogram of the test solution; $A_{std}$ is the area of the Sitagliptin peak in the chromatogram of the standard solution; $W_{std}$ is the accurate weigh of the Sitagliptin working standard used for the preparation of the standard solution (mg); $W_{test}$ is the accurate weigh of the sample used for the preparation of the sample solution (mg); LC is the Label Claim (50 mg/2 ml); d is the density of the formulation sample; and % P is the % purity of the Sitagliptin working standard.

Determination of Impurities:

During manufacture and storage, impurities can be formed, mentioned in table 2 below. The main impurities observed are (R)-3-amino-4-(2,4,5 trifluoro-phenyl)butanoic acid, 3-(trifluorophenyl)-5,6,7,8tetrahydro-[1,2,4]triazolo-[4,3a]-pyrazine hydrochloride and the S-isomer of sitagliptin.

Column: NUCLEOSIL EC 100-5 CN, 250×4.6 mm, 5 μm (Lot: 21606024-SN: N18071524).

Reference solution: Sitagliptin Hydrochloride working standard (Biocon, India, batch Q1/WS/040/02, purity: 99.9%, expiration date Jun. 1, 2020).

Diluent A: ACN/$H_2O$: 5/95

Diluent B: $H_2O$

Reference Sitagliptin solution: 0.001 mg/ml as base or 0.2% of test concentration. An accurately weighted quantity of Sitagliptin HCl working standard of 10.9 mg (equivalent to 10 mg of Sitagliptin base) was transferred into a 20 ml volumetric flask. The envisage volume was obtained by dilution with diluent A followed by vortexing/mixing to homogenize. Of this solution, 0.1 m was transferred into a 50 ml volumetric flask, diluted to volume with diluent B and vortexed/mixed to homogenize.

Test solution: 0.5 mg/ml as base. Of the sample preparation, 2.0 ml were transferred into a 10.0 mL volumetric flask. 10 ml Diluent A was added, followed by vortexing/mixing to dissolve, and the volume was diluted to the envisaged volume with diluent A. Of this solution, 1.0 ml was transferred into a 10 ml volumetric flask, diluted to volume with diluent B and vortexed/mixed to homogenize. The obtained solution was filtrated through a RC 0.45 μm filter and fill in a HPLC vial.

TABLE 2

Impurities

| Impurity Name | Chemical Name/Molecular Formula/Molecular Weight | Structure | Nature of Impurity | Source/ Mechanism | Control |
|---|---|---|---|---|---|
| Impurity A | (R)-3-(tert-butoxycarbonylamino)-4-(2,4,5-trifluorophenyl) butanoic acid | 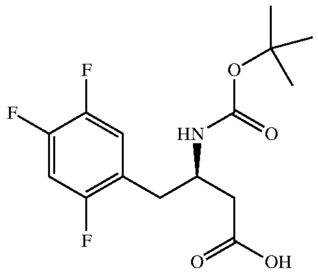 [SMILES: CC(C)(C)OC(=O)N[C@@H](CC(=O)O)Cc1cc(F)c(F)cc1F] | Process related | Unreacted KSM-1 (SBA) | NMT 0.15% |

TABLE 2-continued

Impurities

| Impurity Name | Chemical Name/Molecular Formula/Molecular Weight | Structure | Nature of Impurity | Source/ Mechanism | Control |
|---|---|---|---|---|---|
| Impurity-B | (R)-3-amino-4-(2,4,5-trifluorophenyl) butanoic acid | 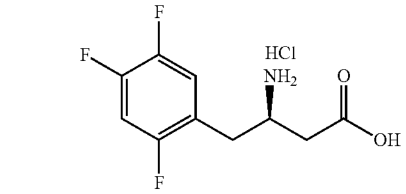 [SMILES: N[C@@H](CC(=O)O)Cc1cc(F)c(F)cc1F ; Cl] | Degradant | BOC deprotected moiety of SBA | NMT 0.15% |
| Impurity-C | 3-(trifluorophenyl)-5,6,7,8-tetrahydro-[1,2,4] triazolo[4,3-a] pyrazine hydrochloride | 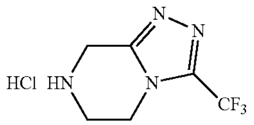 | Degradant | Unreacted KSM-2 (STP) | NMT 0.15% |
| Impurity-D | (R)-tert-butyl-4-oxo-4-(3-(trifluoromethyl)-5,6-dihydro-[1,2,4]triazolo [4,3-a]pyrazin-7(8H)-yl)-1-(2,4,5-trifluorophenyl)butan-2-ylcarbamate | 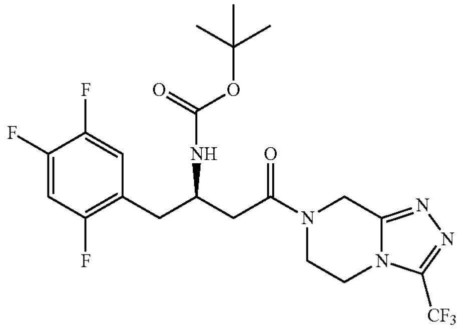 [SMILES: CC(C)(C)OC(=O)N[C@@H](CC(=O)N1CCn2c(nnc2C(F)(F)F)C1)Cc1cc(F)c(F)cc1F] | Process related | Unreacted Intermediate STN-BOC | NMT 0.15% |
| Impurity-F | (Z)-1-(3-(trifluoromethyl)-5,6-dihydro[1,2,4] triazolo[4,3-a]pyrazin-7(8H)-yl]-4-(2,4,5-trifluorophenyl)but-2-en-1-one | 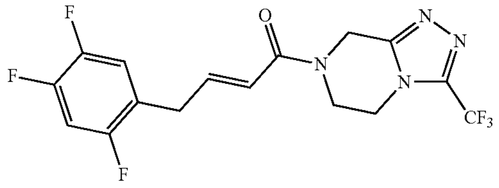 [SMILES: O=C(/C=C/Cc1cc(F)c(F)cc1F)N1CCn2c(nnc2C(F)(F)F)C1] | Process related | Oxidative Impurity | NMT 0.15% |
| S-Isomer content (Impurity E content) | (3S)-3-amino-1-[3-(trifluoromethyl)-5,6-dihydro[1,2,4]triazolo-[4,3-a]pyrazin-7(8H)-yl]-4-(2,4,5-trifluorophenyl)butan-1-one (S-enantiomer) | 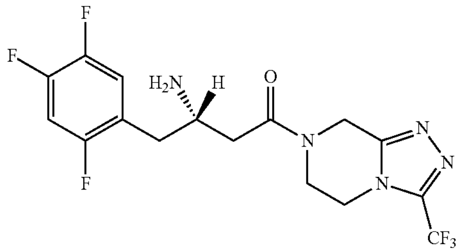 [SMILES: N[C@H](CC(=O)N1CCn2c(nnc2C(F)(F)F)C1)Cc1cc(F)c(F)cc1F] | Process related | Isomer impurity carry over from KSM-1 SBA | NMT 0.15% |

System Suitability Solutions:

Impurity B stock solution: 2 mg of (R)-3-amino-4-(2,4,5 trifluorophenyl)-butanoic acid was transferred into a 20 ml volumetric flask. The envisaged volume was obtained by dilution with diluent A and vortexing/mixing to homogenize.

Impurity C stock solution: 2 mg of 3-(trifluorophenyl)-5, 6,7,8tetrahydro-[1,2,4]triazolo[4,3a]pyrazine hydrochloride was transferred into a 20 ml volumetric flask. The envisaged volume was obtained by dilution with diluent A and vortexing/mixing to homogenize.

0.25 ml of both Impurity B stock solution and of Impurity C stock solution were added into a 10 ml volumetric flask, diluted to volume with diluent B and vortexed/mixed to homogenize.

System suitability criteria: For the Resolution solution, the resolution between Impurity B and Impurity C should be >2.0. The 3 replicates of the standard solution for unknown impurities were used: % RSD≤2.0%.

Mobile Phase:

A: Buffer pH 3.2 was obtained by weighing 1.36 g of potassium dihydrogen phosphate in 1000 mL of Milli-Q water and the pH was adjusted to 3.2 with orthophosphoric acid (85%), followed by filtration through a 0.45 μm membrane filter. B: Acetonitrile for HPLC, gradient grade.

Injection volume: 20 μl; Column temperature and autosampler temperature: 25° C.; Run time: 90 minutes; Quantification wavelength: 205 nm.

Gradient Program:

| Time (min) | Mobile phase A (% v/v) | Mobile phase B (% v/v) | Flow Rate (ml/min) |
|---|---|---|---|
| 0-5 | 99 | 1 | 0.7 |
| 5.01 | 95 | 5 | 0.7 |
| 31.0 | 95 | 5 | 0.7 |
| 31.01 | 80 | 20 | 0.8 |
| 64.0 | 80 | 20 | 0.8 |
| 64.01 | 99 | 1 | 0.7 |
| 90.0 | 99 | 1 | 0.7 |

Calculation of the Sitagliptin Content: By the Equation:

$$\%\ \text{Recovery} = \frac{Asmp \times Vsmp \times Wstd \times Pstd \times Dstd \times 100}{Astd \times LC \times Dsmp \times Vstd}$$

wherein: Asmp is the peak area response of sitagliptin in the sample solution chromatograms; Astd is the average peak area response of sitagliptin in the standard solution chromatograms; LC is the Label Claim of the formulation (=50 mg/2 ml); Wstd is the weight of the Sitagliptin standard in mg; Vsmp is the initial volume of the test solution in ml; Vstd is the initial volume of the standard solution in ml; Pstd is the purity of the standard in decimal form; Dstd is the standard dilution; and Dsmp is the sample dilution.

Under the chromatography conditions as described above, the relative retention time (RRT) for impurity B is 0.37, for impurity C 0.28. The response factor (RF) is 1.58 for impurity B, 3.12 for impurity C and 1.0 for any other impurity.

The product specification of a sitagliptin solution of formula 1 is depicted in table 3.

TABLE 3

| Product specification Solution Formula 1 after production | | | |
|---|---|---|---|
| # | TESTS | METHOD | SPECIFICATIONS |
| 1 | Appearance | Visual inspection | Amber glass bottle with cap |
| 2 | Clarity and degree of opalescence of liquids | Ph. Eur. cur. ed. (2.2.1) | Colourless to nearly colourless liquid |
| 3 | Degree of coloration of the liquids | Ph. Eur. cur. ed. (2.2.2) | Colourless to nearly colourless |
| 4 | pH | Ph. Eur. cur. ed. (2.2.3) | 5.6-5.9 |
| 5 | Relative Density | Ph. Eur. cur. ed. (2.2.5) | 1.00-1.05 |
| 6 | Uniformity of mass of delivered doses | Ph. Eur. cur. ed. (2.9.27) | Meets the requirements |
| 7 | Uniformity of dosage units | Ph. Eur. cur. ed. (2.9.40) | Meets the requirements (MV) |
| 8 | Deliverable Volume | USP <698> | Meets the requirements |
| 9 | Package integrity | In house method | Pass |
| 10 | Identification Sitagliptin HCL | HPLC (UV)<br>HPLC (Diode Array) | Retention time complies with RS<br>UV spectrum complies with RS |
| 11 | Identification BHA, EDTA and methylparaben | HPLC (UV) | Retention time complies with RS |
| 14 | Assay of Sitagliptin HCl | In-house method<br>Ph. Eur. cur. ed. (2.2.29) | 95.0-105.0% of the stated amount of Sitagliptin HCl |
| 15 | Assay of BHA, EDTA and methylparaben | In house method<br>Ph. Eur. cur. ed. (2.2.29) | Each 90.0-110.0% |
| 18 | Related Substances | In house method<br>Ph. Eur. cur. ed. (2.2.29) | 0.1% |
| 19 | Microbial Limits Testing | | |
| | Total Aerobic Microbial Count | Ph. Eur. cur. ed. (5.1.4) | 100 CFU/mL |
| | Total Combined Yeasts/Moulds | | 10 CFU/mL |
| | *E. Coli* | | Absent/1 mL |
| 20 | Antimicrobial Effectiveness Testing | Ph. Eur. cur. ed. (5.1.3) | Pass |

Stability

Stability tests of the 8 formulas of table 1 are depicted in table 4A, wherein the total impurities (i.e. impurities B, C and the other impurities) are indicated as percentage of the initial sitagliptin content. 'nd' stands for 'not detected'.

TABLE 4A

| Stability | | | | | | | | | |
|---|---|---|---|---|---|---|---|---|---|
| | Months | | | | | | | | |
| | | 2 | 3 | 2 | 3 | 1 | 3 | 2 | 3 |
| Formula | 0 | 5° C. | | 25° C.-60% RH | | 30° C.-65% RH | | 40° C.-75% RH | |
| 1 | 0.10 | nd | nd | 0.21 | 0.33 | nd | nd | nd | nd |
| 2 | nd | nd | nd | nd | 0.10 | nd | 0.47 | 0.14 | 2.07 |
| 3 | 0.68 | nd | 0.44 | 0.68 | 0.81 | 0.85 | 1.15 | 1.83 | 2.36 |

TABLE 4A-continued

| Stability | | | | | | | | | |
|---|---|---|---|---|---|---|---|---|---|
| | Months | | | | | | | | |
| Formula | 0 | 2 5° C. | 3 5° C. | 2 25° C.-60% RH | 3 25° C.-60% RH | 1 30° C.-65% RH | 3 30° C.-65% RH | 2 40° C.-75% RH | 3 40° C.-75% RH |
| 4 | 0.37 | nd | 0.14 | 0.51 | 0.53 | 0.70 | 0.82 | 1.89 | 2.74 |
| 5 | 0.79 | nd | 0.52 | 0.99 | 1.06 | 0.91 | 1.67 | 3.41 | 3.88 |
| 6 | 1.18 | nd | 0.37 | 1.05 | 1.19 | 1.69 | 1.86 | 4.27 | 5.84 |
| 7 | 0.97 | nd | 0.75 | 1.16 | 1.33 | 1.43 | 1.81 | 2.36 | 2.93 |
| 8 | 0.41 | nd | 0.13 | 2.67 | 3.61 | 0.66 | 0.69 | 2.67 | 3.61 |

From table 1 it can be observed that formulas 1 and 2 appeared to be the most stable at 25° C. and formula 2 at intermediate conditions 3000 and a humidity of 65% and at accelerated conditions of 4000 and a humidity of 75% after 2 and 3 months. The difference between formulas 1 and 2 is the presence of propylene glycol, that has a positive effect on preservation, see table 6A. The total impurities after 2 months at 2500 and a relative humidity of 60% were less than 0.30% for formula 1, and after three months even as low as 0.10 for formula 2.

Formulas 3 to 8 were less stable as compared to formulas 1 and 2. Formulas 1, 2, 4, 6 and 8 comprises BHA as antioxidant, and for that reason these formulas contained some Polysorbate 80. Formulas 3, 5 and 7 are identical to formulas 4, 6 and 8, except that instead of BHA/Polysorbate metabisulphite was used as antioxidant. Formula 4 differs from formula 2 in sweetener content.

The stability of formula 2 was further measured at both 5° C. and 25° C. for 6 and 9 months and shown in table 4B. In table 4B3, 'ND' stands for 'Not Detected', and 'BRT' for 'Below the Retention Limit of the analytical equipment'.

The total impurities after six months at 25° C. and a relative humidity of 60% were less than 0.70% and after nine months less than 1.0%.

TABLE 4B

| Extended Stability Formula 2 | | | | | |
|---|---|---|---|---|---|
| | | 5 °C RH 60% | | 25 °C RH 60% | |
| | | 6M | 9M | 6M | 9M |
| Appearance | Specification | Complies | Complies | Complies | Complies |
| Assay sitagliptin % | 95-105% | 987 | 100.6 | 100.0 | 100.0 |
| Any other impurity % | NMT 0.2% | ND | ND | ND | ND |
| Impurity B | NMT 0.5% | BRT | BRT | 0.34 | 0.48 |
| Impurity C | NMT 0.5% | BRT | BRT | 0.31 | 0.45 |
| Total impurities % | NMT 1.5% | ND | ND | 0.65 | 0.93 |
| pH | 4.5-6.5 | 5.8 | 5.7 | 5.7 | 5.7 |
| Density (g/ml) | ND | 1.02 | 1.03 | 1.03 | 1.03 |

In Table 4C the stability of some modifications of formula 2 and of sample R5B were determined after 2 and 4 months at both 5° C. and 25° C. In table 4C, 'ND' stands for 'Not Detected', and 'BRT' for 'Below the Retention Limit of the analytical equipment'. Formula 2B is identical to formula 2, wherein the antioxidant is 0.1 v/w metabisulphite instead of BHA and does not contain polysorbate. Accordingly, formula 2B corresponds with formula 3 of table 2, now having 2 w/v % sweetening/flavouring of the product sold under the trade name POLISUCRA mix. Formula 2A corresponds with formula 2 but lack antioxidant. Formula 2AT lacks both antioxidant and thickener. Formula R5B is the formula of example 5b of WO2015/044880, i.e. having 45 w/v % xylitol, 0.2 v/w % sucralose without any antioxidant.

The total impurities for formula 2B after 4 months were below the detection limit and less than 0.55% after 4 months at 25° C. and a relative humidity of 60%. The absence of antioxidant does not seem to have an effect on stability, as similar results are obtained for formula 2A. Interestingly, the absence of thickener results in precipitation in the composition (downward arrow), resulting in a decrease of measurable sitagliptin of about 50% after 2 months at 25° C. and

TABLE 4C

| Stability | | | | | | | | | | |
|---|---|---|---|---|---|---|---|---|---|---|
| | | Formula 2B | | Formula 2A | | Formala 2AT | | Formula R5B | | |
| | Specification | 2M | 4M | 2M | 4M | 2M | 4M | 0M | 2M | 4M |
| 25° C. | | | | | | | | | | |
| Appearance | clear solution | Complies | Complies | Complies | Complies | ↓ | ↓↓↓ | Complies | Complies | Complies |
| Assay sitagliptin % | 95-105% | 98.8 | 102.3 | 103.9 | 102.5 | 50.1 | NP | 101.1 | 96.9 | 100.1 |
| Any other impurity % | NMT 0.2% | ND | ND | ND | ND | ND | NP | ND | ND | ND |
| Impurity B | NMT 0.5% | BRT | 0.33 | 0.1 | 0.20 | 0.05 | NP | BRT | 0.33 | 0.33 |
| Impurity C | NMT 0.5% | ND | 0.17 | 0.13 | 0.32 | ND | NP | ND | 0.31 | 0.0 |
| Total impurities % | NTM 1.5% | BRT | 0.51 | 0.23 | 0.52 | 0.05 | NP | BRT | 0.64 | 0.63 |
| pH | 4.5-6.5 | 5 | 5.0 | 5.7 | 5.7 | 5.7 | NP | 5.9 | 6.2 | 5.5 |
| Density (g/ml) | ND | 1.02 | 1.02 | 1.02 | 1.01 | 1.04 | NP | 1.15 | 1.16 | 1.15 |
| 5° C. | | | | | | | | | | |
| Appearance | clear splotion | Complies | Complies | Complies | Complies | ↓ | ↓↓↓ | Complies | Complies | Complies |
| Assay sitagliptin % | 85-105% | 97.4 | 99.3 | 103.7 | 99.3 | 43.6 | NP | 101.1 | 98.9 | 102.5 |
| Any other impurity % | NMT 0.2% | ND | ND | ND | ND | ND | NP | ND | ND | ND |
| Impurity B | NMT 0.5% | BRT | 0.05 | BRT | 0.05 | ND | NP | BRT | BRT | BRT |
| Impurity C | NMT 0.5% | ND | BRT | ND | BRT | ND | NP | ND | BRT | BRT |
| Total Impurities % | NMT 1.5% | BRT | 0.05 | BRT | 0.05 | ND | NP | BRT | BRT | BRT |
| pH | 4.5-6.5 | 4.8 | 4.3 | 5.8 | 4.3 | 5.5 | NP | 5.9 | 6.3 | 6.1 |
| Density (g/ml) | ND | 1.01 | 1.03 | 1.05 | 1.03 | 1.02 | NP | 1.15 | 1.17 | 1.15 |

even more at 5° C. After 4 months, the precipitation was increased such, that no measurements could be taken (three downward arrows). This observation may be an indication that the presence of thickener may be important for the stability of the composition. However, the total impurities content does not increase accordingly, as would be expected.

It is interesting to observe that formula R5B is rather stable, having however more impurities both after 2 and 4 months as compared with formulas 2A and 2B. This stability may be due to the high xylitol content, that may have a stabilizing effect on the composition.

Taste Assessment

In order to assess the taste of the compositions, tasting panel of 6-8 persons tasted the compositions. The panel evaluated formulas 1 and 2 as most attractive. Formulas 5-8 were evaluated to be unattractively bitter, that may be due to the sugar alcohols present in these formulas. Further, was observed that an increased level of polyols (formulas 5 and 6) did not improve the taste as compared to formulas 7 and 8, comprising lower levels of polyols.

In an additional taste assessment, the tasting panel tasted 23 different formulations, 21 of which were identical to formula 2, except for the amount and type of thickener.

Sample 3 corresponds with formula 2 of table 1. Sample 4 is identical to sample 3, except for the sweetening mix. Formula 3 has the product sold under the trade name POLISUCRA 7477, whereas sample 4 has the product sold under the trade name POLISUCRA 7478 in the identical amount. The difference lies in the sweeteners: formula 2 comprises 1.105 w/v % sucralose and 0.595 w/v % sodium saccharin, whereas sample 4 has 1.3 w/v % sucralose and 0.4 w/v % acesulfame K. Accordingly, the sweetening power of formula 2 (and all samples 1-21 except for sample 4) corresponds with 871 w/v % saccharose and that of sample 4 corresponds with 860 w/v % sweetening power.

Sample 22 again corresponds with the composition of example 5b of WO2015/044880, and sample 23 comprises the amount and type of thickener as formula 2 (0.4 w/v %). Both formulas 22 and 23 have a sweetening power corresponding with 165 w/v % saccharose.

The panel evaluated the taste by scoring each taste sample from 1 to 5, 1 being totally unacceptable, and 5 being very tasteful. The average values of the taste panel member are given in table 5.

Interestingly, sample 22, i.e. the composition of example 5b of WO2015/044880 was evaluated as very unattractive (an average score of 1.3). Additional thickener improved the taste somewhat, but it was still unacceptable (an average score of 1.9).

Sample 21, being identical to that of formula 2, but without thickener, has an average score of 2.7, i.e. significantly higher than those of samples 22 and 23. For each thickener, it can be observed that a taste improvement is achieved as compared to sample 21 (without thickener), but for the plurality of thickeners, there is a level above which the score decreases to even below that of the score of sample 21. It is believed that an increase in thickener above a critical point, which point differs for each thickener, results in less attractive mouthfeel. It is observed that addition of thickener increases the taste-masking as compared to a similar sample without thickener. The presence of sugar alcohols but also that of other polyols and polyalkylene glycols (data not shown) appear to have a negative impact on the taste of gliptin composition and the off-taste of such compositions is difficult if not impossible to mask.

TABLE 5

| Taste assessment | | |
|---|---|---|
| 1 | Hydroxyethylcellulose 0.8% | 3.7 |
| 2 | Hydroxyethylcellulose 0.6% | 3.3 |
| 3 | Hydroxyethylcellulose 0.4% | 3.2 |
| 4 | Hydroxyethylcellulose 0.4%-Polisucra 7478 | 4.1 |
| 5 | Hydroxyethylcellulose-0.2% | 2.9 |
| 6 | Hydroxyethylcellulose 0.1% | 3.5 |
| 7 | Sodium alginate 0.4% | 2.1 |
| 8 | Sodium alginate 0.2% | 3.5 |
| 9 | Hydroxypropylcellulose 0.3% | 2.4 |
| 10 | Hydroxypropylcellulose 0.2% | 5.1 |
| 11 | Hydroxypropylcellulose 0.1% | 3.1 |
| 12 | Gellan Gum 0.3% | 2.4 |
| 13 | Gellan Gum 0.2% | 3.3 |
| 14 | Gellan Gum 0.1% | 2.9 |
| 15 | Carboxymethylcellulose 0.4% | 2.5 |
| 16 | Carboxymethylcellulose 0.2% | 2.8 |
| 17 | Carboxymethylcellulose 0.1% | 2.7 |
| 18 | Polyethylene oxide polymer 2.0% | 3.6 |
| 19 | Polyethylene oxide polymer 1.0% | 4.5 |

TABLE 5-continued

| Taste assessment | | |
|---|---|---|
| 20 | Polyethylene oxide polymer 0.5% | 2.8 |
| 21 | No thickener | 2.7 |
| 22 | Formula R5B | 1.3 |
| 23 | Formula R5B + HEC 0.4% | 1.9 |

Antimicrobial Preservation

Formulas 1, 2 and R5B were tested for efficacy of antimicrobial preservation according to the teaching of the European Pharmacopeia 9.0, section 5.1.3, pp 577 ff. by Quality Assurance & Control Systems Ltd., Athens, Greece. The test consists of challenging the sample solution with a prescribed inoculum of suitable micro-organisms as shown in the tables 6A-C, storing the inoculated solution at ambient temperature, avoiding sunlight, withdrawing samples from the container at specified intervals of time and counting the micro-organisms in the samples so removed. The preservative properties of the solution are adequate if, in the conditions of the test, there is a significant fall or no increase, as appropriate, in the number of micro-organisms in the inoculated solution after 14 and 28 days. ATCC stands for the deposit number of the micro-organism at the American Type Culture Collection ATCC.

The count of *Aspergillus brasiliensis* is lower for formula 1 after 27 days as compared to formula 2, but both samples comply with the requirement. This in contrast with sample R5B, showing unacceptably high counts for *Aspergillus brasiliensis* after 14 and 27 days (both $1.7 \times 10^5$).

TABLE 6A

Preservation efficacy on Formula 1

| Micro-organism | ATCC | Lot | Inoculation Cfu/g | Time zero | Day 14 | Day 27 |
|---|---|---|---|---|---|---|
| *Pseudomonas aeruginosa* | 9027 | 4847054 | $3.1 \times 10^6$ | <10 | <10 | <10 |
| *Staphylococcus aureus* | 6538 | 4854821 | $3.8 \times 10^6$ | $2.8 \times 10^6$ | <10 | <10 |
| *Escherichia coli* | 8739 | 4835664 | $5.1 \times 10^6$ | <10 | <10 | <10 |
| *Candida albicans* | 10231 | 4435903 | $4.2 \times 10^6$ | $3.8 \times 10^6$ | <10 | <10 |
| *Aspergillus brasiliensis* | 16404 | 3925233 | $2.8 \times 10^6$ | $2.3 \times 10^6$ | $2.4 \times 10^3$ | 9.1 × 102 |

TABLE 6B

Preservation efficacy on Formula 2

| Micro-organism | ATCC | Lot | Inoculation Cfu/g | Time zero | Day 14 | Day 27 |
|---|---|---|---|---|---|---|
| *Pseudomonas aeruginosa* | 9027 | 4847054 | $3.1 \times 10^5$ | <10 | <10 | <10 |
| *Staphylococcus aureus* | 6538 | 4854821 | $3.8 \times 10^5$ | $3.4 \times 10^5$ | <10 | <10 |
| *Escherichia coli* | 8739 | 4835664 | $5.1 \times 10^5$ | <10 | <10 | <10 |
| *Candida albicans* | 10231 | 4435903 | $4.2 \times 10^5$ | $3.6 \times 10^5$ | <10 | <10 |
| *Aspergillus brasiliensis* | 16404 | 3925233 | $2.8 \times 10^5$ | $2.2 \times 10^5$ | $2.4 \times 10^3$ | $3.3 \times 10^3$ |

TABLE 6C

Preservation efficacy on Formula R5B

| Micro-organism | ATCC | Lot | Inoculation Cfu/g | Time zero | Day 14 | Day 27 |
|---|---|---|---|---|---|---|
| *Pseudomonas aeruginosa* | 9027 | 4847054 | $6.0 \times 10^5$ | $3.7 \times 10^3$ | <10 | <10 |
| *Staphylococcus aureus* | 6538 | 4854821 | $8.2 \times 10^5$ | $7.6 \times 10^5$ | <10 | <10 |
| *Escherichia coli* | 8739 | 4835664 | $6.8 \times 10^5$ | $6.3 \times 10^5$ | <10 | <10 |
| *Candida albicans* | 10231 | 4435903 | $5.2 \times 10^5$ | $4.7 \times 10^5$ | <10 | <10 |
| *Aspergillus brasiliensis* | 16404 | 3925233 | $3.8 \times 10^5$ | $3.5 \times 10^5$ | $1.7 \times 10^5$ | $1.7 \times 10^5$ |

It has now been found that sitagliptin solutions can be obtained with high stability and antimicrobial efficacy with an attractive taste, therewith providing an attractive alternative to sitagliptin in the form of tablets and to known liquid sitagliptin compositions that have an unacceptable off-taste. It is believed that the thickener in the composition may both have a positive effect on organoleptic experience, as well as on the stability of the solution. The sitagliptin solution of WO2015/044880 has a high sugar alcohol content and is void of any thickener and does not have the stability of the formulas as described herein.

The invention claimed is:

1. An aqueous liquid oral gliptin composition comprising:

about 2.5-about 3.5 w/v % of sitagliptin or a pharmaceutically acceptable salt or ester thereof;

a thickening agent, wherein the thickening agent is selected from the group consisting of hydroxyethylcellulose, hydroxypropylcellulose, sodium alginate, sodium carboxymethylcellulose, gellan gum, polyethylene oxide polymer, xanthan gum, acacia, guar gum, locust bean gum, gum tragacanth, starch, carbopols, methylcellulose, polyvinylpyrrolidone, and any combination thereof, wherein the thickening agent is present in the aqueous liquid oral gliptin composition at about 0.1-about 2.0 w/v %;

an artificial non-sugar alcohol sweetening agent, wherein the artificial non-sugar alcohol sweetening agent is present in the aqueous liquid oral gliptin composition at 1-5 w/v %;

wherein the aqueous liquid oral gliptin composition has a sugar alcohol content of less than 20 w/v %;

a buffering agent; and a preservative;

and wherein the pH of the aqueous liquid oral gliptin composition is from 3 to 8.

2. The aqueous liquid oral gliptin composition of claim 1, wherein the sitagliptin is in the form of a chloride or a phosphate salt.

3. The aqueous liquid oral gliptin composition of claim 1, wherein the thickening agent is selected from the group consisting of hydroxyethylcellulose, hydroxypropylcellulose, sodium carboxymethylcellulose, and any combination thereof.

4. The aqueous liquid oral gliptin composition of claim 1, wherein the thickening agent is present in the aqueous liquid oral gliptin composition at about 0.1-about 0.8 w/v %.

5. The aqueous liquid oral gliptin composition of claim 1, wherein the thickening agent is present in the aqueous liquid oral gliptin composition at about 0.4-about 0.6 w/v %.

6. The aqueous liquid oral gliptin composition of claim 1, wherein the artificial non-sugar alcohol sweetening agent is selected from the group consisting of sucralose, sodium saccharin, aspartame, acesulfame-K, cyclamate, alitame, stevioside, glycyrrhizin, neohesperidin, dihydrochalcone, thaumatin, and any combination thereof.

7. The aqueous liquid oral gliptin composition of claim 6, wherein the artificial non-sugar alcohol sweetening agent is a combination of sucralose and sodium saccharin, or a combination of sucralose and acesulfame-K.

8. The aqueous liquid oral gliptin composition of claim 7, wherein the sucralose is present in the aqueous liquid oral gliptin composition at about 0.8-about 2.0 w/v %.

9. The aqueous liquid oral gliptin composition of claim 7, wherein the acesulfame-K is present in the aqueous liquid oral gliptin composition at about 0.2-about 1.0 w/v %.

10. The aqueous liquid oral gliptin composition of claim 1, wherein the buffering agent comprises a citrate.

11. The aqueous liquid oral gliptin composition of claim 1, wherein the buffering agent is present in the aqueous liquid oral gliptin composition at about 0.1-about 1.0 w/v %.

12. The aqueous liquid oral gliptin composition of claim 1, wherein the pH of the aqueous liquid oral gliptin composition is from 4 to 7.

13. The aqueous liquid oral gliptin composition of claim 1, wherein the preservative is selected from the group consisting of methyl paraben, ethyl paraben, propyl paraben, butyl paraben, any combination thereof, and any salt thereof.

14. The aqueous liquid oral gliptin composition of claim 1, wherein the preservative is present in the aqueous liquid oral gliptin composition at about 0.1-about 0.5 w/v %.

15. The aqueous liquid oral gliptin composition of claim 1, further comprising a chelating agent, and wherein the chelating agent is selected from the group consisting of disodium edentate salt, tartaric acid, malic acid, citric acid, and any combination thereof.

16. The aqueous liquid oral gliptin composition of claim 1, further comprising a wetting agent, and wherein the wetting agent is selected from the group consisting of sorbitan esters of fatty acids, sorbitan monolaurate, sorbitan monooleate, sorbitan trioleate, fatty alcohol-polyethylene glycol ethers, polysorbate 80, and any combination thereof.

17. The aqueous liquid oral gliptin composition of claim 1, further comprising a flavouring agent.

18. The aqueous liquid oral gliptin composition of claim 17, wherein the flavouring agent is selected from the group consisting of forest fruits flavour, strawberry, raspberry, cherry, cranberry, blueberry, black currant, red currant, gooseberry, lingonberries, and any combination thereof.

19. The aqueous liquid oral gliptin composition of claim 1, wherein the aqueous liquid oral gliptin composition has a sugar alcohol content of less than 10 w/v %.

20. The aqueous liquid oral gliptin composition of claim 19, wherein the aqueous liquid oral gliptin composition has a sugar alcohol content of less than 5 w/v %.

21. The aqueous liquid oral gliptin composition of claim 1, wherein the aqueous liquid oral gliptin composition comprises at less than 1% total impurities after storage of 9 months at 25° C. and 60% humidity.

22. The aqueous liquid oral gliptin composition of claim 1, wherein the aqueous liquid oral gliptin composition comprises at least 95% of the gliptin or a pharmaceutically acceptable salt or ester thereof after storage of 18 months at 25° C. and 60% humidity.

* * * * *